US006916969B1

(12) United States Patent
Helmfridsson et al.

(10) Patent No.: US 6,916,969 B1
(45) Date of Patent: Jul. 12, 2005

(54) MATERIAL LAMINATE FOR USE AS A COVERING SHEET IN AN ABSORBENT ARTICLE

(75) Inventors: Bror-Inge Helmfridsson, Partille (SE); Urban Nilsson, Kungälv (SE); Stefan Lindgren, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 361 days.

(21) Appl. No.: 10/019,955

(22) PCT Filed: Jul. 3, 2000

(86) PCT No.: PCT/SE00/01405

§ 371 (c)(1),
(2), (4) Date: Jan. 7, 2002

(87) PCT Pub. No.: WO01/03626

PCT Pub. Date: Jan. 18, 2001

(30) Foreign Application Priority Data

Jul. 9, 1999 (SE) .................................... 9902647

(51) Int. Cl.$^7$ ............................................. A61F 13/20
(52) U.S. Cl. ...................... 604/378; 604/370; 604/366
(58) Field of Search ............................... 604/365, 366, 604/370, 378

(56) References Cited

U.S. PATENT DOCUMENTS 3,924,626 A * 12/1975 Lee et al. .................... 604/366
4,761,322 A 8/1988 Raley (Continued)

FOREIGN PATENT DOCUMENTS

| EP | 685214 | 12/1995 |
|----|--------|---------|
| EP | 617602 | 3/1997 |
| WO | 93/11725 | 6/1993 |
| WO | 98/27904 | 7/1998 |
| WO | 99/49825 | 10/1999 |

Primary Examiner—Larry I. Schwartz
Assistant Examiner—Linh Truong
(74) Attorney, Agent, or Firm—Burns, Doane, Swecker & Mathis, L.L.P.

(57) ABSTRACT

The invention relates to a material laminate for use as a covering sheet on absorbent articles such as sanitary napkins, incontinence protectors, diapers, pant diapers, or the like. The material laminate comprises a first, fluid pervious fibrous material layer and a second fluid pervious porous material layer, wherein at least one of the two material layers comprises thermoplastic material and wherein the two material layers are mutually connected by means of the covering material laminate exhibiting bond sites within which the thermoplastic material has been caused to at least partially soften or melt and thereby bond the two material layers together. In the planar extension, the material laminate exhibits two side portions extending in the length direction and having an extension in the width direction from a respective longitudinal side edge and a distance in towards the longitudinal central axis of the material laminate and a central portion positioned between the side portions in the planar extension of the material laminate, wherein the first material layer and the second material layer in the central portion of the material laminate are intermittently bonded together with a first bond pattern and that the first material layer and the second material layer in the two side portions of the material laminate are intermittently bonded together with a second bond pattern wherein the percentage bonded area in relation to the total area in the two side portions is greater then the percentage bonded area in relation to the total area in the central portion. The invention further pertains to an absorbent article comprising the material laminate.

28 Claims, 4 Drawing Sheets

U.S. PATENT DOCUMENTS 5,591,149 A * 1/1997 Cree et al. .................. 604/378
5,681,300 A * 10/1997 Ahr et al. ................... 604/367
5,954,705 A * 9/1999 Sawaki et al. ........ 604/385.101
6,103,953 A * 8/2000 Cree et al. .................. 604/365

* cited by examiner

MATERIAL LAMINATE FOR USE AS A COVERING SHEET IN AN ABSORBENT ARTICLE

TECHNICAL FIELD

The present invention relates to a material laminate for use as a covering sheet for absorbent articles such as sanitary napkins, incontinence protectors, diapers, pant diapers, or the like. The material laminate comprises a first, fluid pervious fibrous material layer and a second fluid pervious porous material layer, wherein at least one of the two material layers comprises thermoplastic material and wherein the two material layers are mutually connected by means of the covering material laminate exhibiting bond sites within which the thermoplastic material has been caused to at least partially soften or melt and thereby bond the two material layers together. The invention also pertains to an absorbent article comprising the material laminate.

BACKGROUND OF THE INVENTION

For fluid permeable covering sheets for absorbent articles of this kind, which in use are intended to be in contact with the body of a user, high demands are put on both softness and dryness.

However, it has proven difficult to accomplish a fluid permeable covering sheet having a soft, textile-like surface which remains dry even after repeated wetting when the covering sheet is being used on an absorbent article.

It is known to use nonwoven materials in order to achieve a soft and smooth surface on an absorbent article. In order to obtain a dry surface closest to the skin of a user, it is also known to use hydrophobic nonwoven materials which have been perforated so as to create apertures in the material which are larger than the interstices between the fibres in the nonwoven material.

Thereby, the fluid is passed through the perforated apertures, through the covering material and down to an underlying absorbent material layer.

In order to bond the covering sheet to an inside layer, it is common to use adhesive. However, the adhesives which are available at the present time are usually relatively hydrophobic, implying that fluid transfer from the covering sheet to the inside layer is hindered. When using a more hydrophilic adhesive, there is a risk that the adhesive will migrate into the hydrophobic nonwoven layer closest to the user which will cause the surface closest to the user to be perceived as wet after a first fluid insult. Another problem in connection with adhesively bonded material laminates wherein one of the layers are perforated is that the adhesive in the perforations may irritate the skin of the user during use. It is also a problem in the manufacture of the laminate that there is a risk that adhesive which happens to be applied in the perforations may be transferred to the transport band of the machine. A further problem in connection with absorbent articles exhibiting a perforated covering sheet which is adhered to an inner layer, is the risk of adhesive penetration when the articles are folded after manufacturing.

It is further known, for instance from EP 0,685,214 and EP 0,617,602 to bind together the covering sheet with an inside layer by melting the layers together in a bond pattern. In EP 0,617,602, a covering sheet consisting of a film is thermally bonded to an inside material layer by melting the layers together within specific bond areas. The bonds may, for instance, be circular bond sites.

However, it has been discovered that the covering sheet and the inside layer loose volume and thereby softness and skin friendliness by thermal bonding.

Furthermore, the thermal bonds make the surface of the covering sheet more stiff and thereby less comfortable to carry in direct contact with skin. Since the bonds reduce the volume, i.e. the thickness, of the covering sheet and the inside layer, the distance between the absorption body of the article and the body of the user is also reduced. This means that the risk of fluid penetrating back out of the article and wetting the body of the user is increased. It has also been discovered that the thermal bonds affect the fluid uptake in the covering sheet closest to the user so that the surface closest to the user's body is perceived as being wet after a first fluid insult.

Another problem when using absorbent articles of the above-mentioned kind is that they are exposed to different kinds of mechanical stress. Accordingly, in order to minimise the risk that the constituting layers are separated from each other during use, it is important that the layers in the absorbent article are sufficiently strongly attached to each other.

Furthermore, the bonding should be such that the fluid transfer ability between the constituting layers is good, that the article exhibits low rewet and high softness and conformability.

DESCRIPTION OF THE INVENTION

The problem with accomplishing an absorbent article which can withstand mechanical stress and at the same time exhibit a fluid pervious covering sheet which is soft and comfortable against skin and still exhibits high surface dryness has been substantially removed by the present invention.

A material laminate in accordance with the invention, for use as a fluid pervious covering sheet on absorbent articles such as, for instance, a sanitary napkin, an incontinence protector or a diaper is primarily distinguished in that the material laminate, in its planar extension, exhibits two side portions extending in the length direction and each extending a distance in the transverse direction from a side edge towards the longitudinal central axis of the material laminate and a central portion positioned between the side portions in the planar extension of the material laminate. The first material layer and the second material layer in the central portion of the material laminate are intermittently bonded together in a first bond pattern and the first material layer and the second material layer in the two side portions of the material laminate are intermittently bonded together in a second bond pattern. Further, the percentage bonded area in relation to the total area in the two side portions is greater then the percentage bonded area in relation to the total area of the central portion.

The invention further concerns an absorbent article exhibiting a substantially elongated shape with a planar extension, a length direction, a width direction and a thickness direction and exhibiting a central axis extending in the length direction and two opposing side edges extending in the length direction. The absorbent article comprises a fluid pervious covering sheet, a fluid impervious covering sheet and an absorption body enclosed between the two covering sheets. The absorbent article comprises a material laminate in accordance with the previous description, wherein the material laminate, in a central portion extending in the length direction, exhibits the first bond pattern and the material laminate in the longitudinally extending side portions of the absorbent article exhibits the second bond pattern. In addition, the percentage bonded area in relation to the total area in the two side portions is greater then the percentage bonded area in relation to the total area in the central portion. The central portion extends in the length direction of the article over the whole of the length of the article and the two side portions extend in the length direction of the article over the whole of the length of the article.

With a covering sheet in accordance with the invention, it has shown to be considerably less risk of the two constituting layers separating from each other. Since the risk of the layers separating from each other is reduced, this also brings about a reduction of the risk of leakage. Another advantage with the invention is that the user's visual impression of the article is improved when the material layers are kept together along the longitudinal side edges of the article. The advantage with the surface closest to the user in the longitudinal central portion of the article not exhibiting as great a proportion of bonded area as the longitudinal side portions is that the covering sheet becomes softer and more comfortable to wear in contact with skin. A further advantage is that the risk of the central portion taking up liquid at the bond sites is considerably reduced.

In order to obtain the previously mentioned advantages with a covering sheet comprising a material laminate in accordance with the invention, the material laminate in accordance with a preferred embodiment exhibits a proportion of bonded area in relation to the total area in the central portion which is at least 0.5% less than the proportion of bonded area in relation to the total area in the side portions.

In accordance with one embodiment, the proportion of bonded area in the side portions is at least 3% but preferably more than 5%.

In accordance with another embodiment, the proportion of bonded area in relation to the total area in the central portion is between 3% and 6% and the proportion of bonded area in relation to the total area in the side portions is between 5% and 8%. This embodiment has been shown to be advantageous since the material layers both in the side portions and in the central portions should be sufficiently strongly attached to each other in order to keep air from intruding between the layers and lower the fluid transfer ability, but at the same time the proportion of bonded area must not be so great so that the covering sheet will take up fluid at the bond sites to such an extent so as to make the surface feel wet after a first wetting. Particularly in the central portion, the proportion of bonded area is dependent on the thickness and the density of the material layers constituting the material laminate. For thin and dense material layers, the proportion of bonded area is preferably greater than for material layers, which are somewhat bulkier and thicker.

In accordance with one embodiment, both the first material layer and the second material layer are relatively thin. Preferably, the first material layer exhibits a basis weight of 27 g/m$^2$ or less and the second material layer exhibits a basis weight of 35 g/m$^2$ or less. The advantage with such an embodiment is that the materials closest to the bond sites only exhibit a densified structure to a very limited extent in comparison with the structure of the material layer outside of the area closest to the bond sites. This means that the tendency of the bond sites attracting fluid by capillary action is comparatively restricted.

In accordance with one embodiment, each bond site exhibits a smallest direction of extension and a second direction of extension which is perpendicular to the smallest direction of extension wherein the smallest direction of extension is less than 0.8 millimeters, at least in the first bond pattern. In accordance with a still more preferred embodiment, the smallest direction of extension is 0.3 millimeters or less, at least in the first bond pattern. The said embodiments are advantageous since it has been shown that when the bond sites exceed a certain size, the risk is greater that fluid will be taken up in the material laminate, in and around the bond sites. In order to achieve sufficient anchoring between the layers, i.e. avoid that air exists between the layers and diminishes the contact between them, it has further proven more advantageous to have a greater number of small bond sites than a smaller number of bond sites with a larger bond area.

The material laminate is preferably in the form of a coherent, continuous web wherein the central portion and the side portions extend continuously in the length direction of the continuous web. Such a material laminate is comparatively easy and rational to produce in a continuous process and may, further, be used as a covering sheet on an absorbent article without any particular synchronisation problems.

In accordance with a preferred embodiment, the first bond pattern extends over the full length of the article and also the second bond pattern over all of the length of the two side portions of the article. In such an embodiment, the proportion of bonded area in the central portion is the same over the full length of the article, i.e. the surface of the central portion of the covering sheet which in the plane of the article is situated closest to the transversely extending end edges of the article does also exhibit a smaller proportion of bonded area than the proportion of bonded area in the longitudinally extending side portions. The advantage with such an embodiment is that the manufacture of an absorbent article with such a covering sheet is simpler due to less synchronisation problems. Synchronisation in relation to the absorption body does only have to be made in the length direction of the absorption body. A further advantage is that, when bonding together the material laminate for use as a covering sheet for absorbent articles, the same patterned roller can be used for different sizes of the absorbent article.

In accordance with one embodiment, the side portions are 4 millimeters wide or more along all of the length of the article. Furthermore, the central portion exhibits the same width in the width direction over all of the length of the central portion. Since the crotch portion of the article is somewhat smaller in the width direction than the two end portions of the article, this implies that the side portions are narrowest in the crotch portion and are somewhat wider in the end portions of the article.

In accordance with one embodiment, the bond sites comprise spot bonds.

In accordance with another embodiment, the second bond pattern is more dense than the first bond pattern. This implies that the distance between the bond sites in the second bond pattern is smaller than the distance between the bond sites in the first bond pattern.

In accordance with one embodiment, both the first material layer and the second material layer are relatively thin. Preferably, the first material layer exhibits a basis weight of 27 g/m$^2$ or less and the second material layer exhibits a basis weight of 35 g/m$^2$ or less. The advantage with such an embodiment is that the materials closest by the bond sites only to a very limited extent exhibit a densified structure when compared to the structure of the material layer outside of the area closest to the bond sites. This means that the tendency of the bond sites attracting fluid by capillary action is comparatively restricted.

DETAILED DESCRIPTION OF EMBODIMENTS

Figure 1:
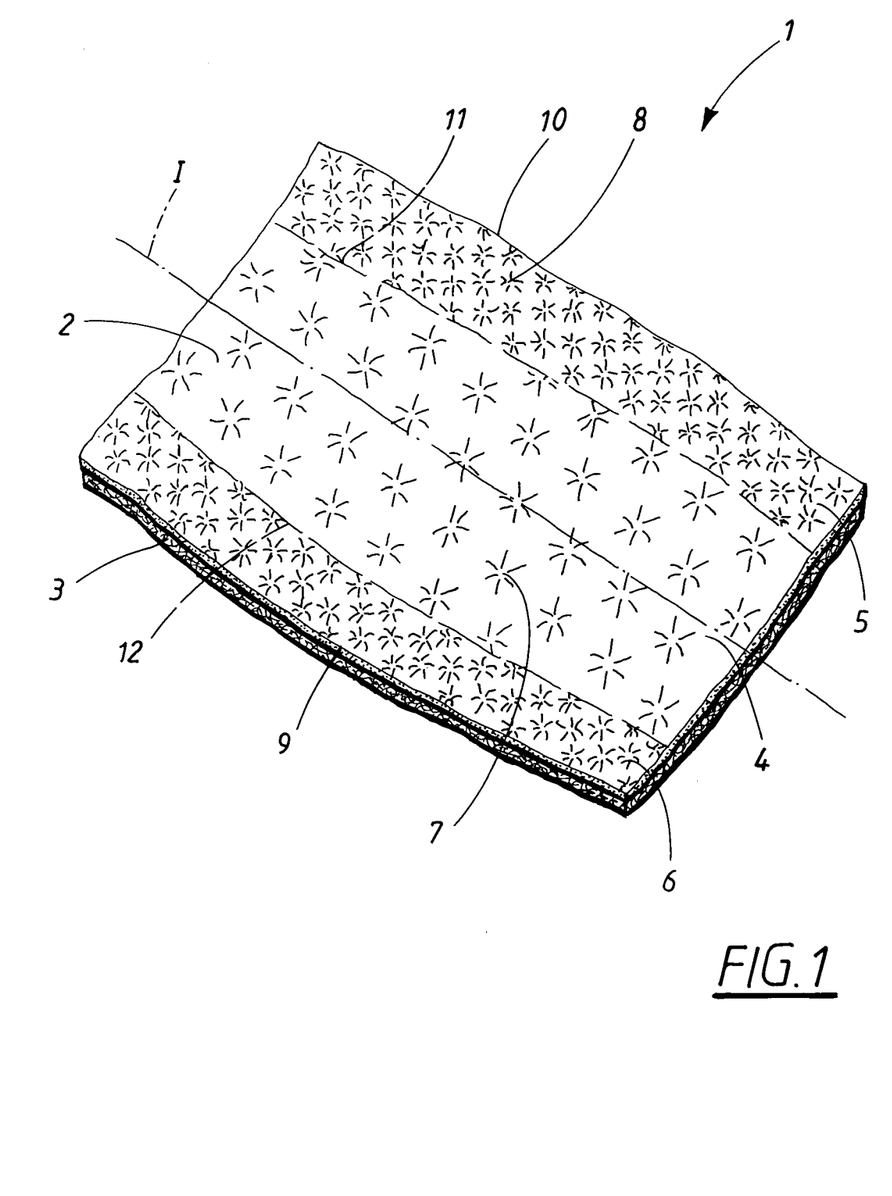
FIG. 1 shows a planar view of a material laminate in accordance with the invention, with a first bond pattern.

The material laminate 1, which is shown in FIG. 1, comprises a first fluid pervious fibrous material layer 2 and a second fluid pervious porous material layer 3. At least the first material layer 2 but preferably both material layers 2,3 comprises thermoplastic material. Suitable thermoplastic materials are polyolefins such as polyethylene and polypropylene and polyamides, polyesters or the like. Further, different kinds of bicomponent fibres can be used. The two material layers 2,3 are mutually connected by bond sites in the material laminate 1 where the two material layers 2,3 have been compressed and the thermoplastic material has been at least partially softened and/or melted.

The material laminate 1 exhibits a planar extension, a length direction, a width direction and a thickness direction. The material laminate 1 exhibits a central axis extending in the length direction and two opposing longitudinal side edges 9,10 extending in the length direction. In the thickness direction, the material laminate comprises a first fluid pervious fibrous material layer 2 and a second fluid pervious porous material layer. A central portion 4 extends from the longitudinal central axis of the material laminate and a distance out towards each longitudinal side edge. Two longitudinal centre lines 11,12 delimit the central portion 4. A side portion 5,6 extends from each centre line 11,12 of the central portion 4, towards each of the longitudinal side edges 8,9 of the material laminate, respectively. The material layers 2,3 in the central portion 4 of the material laminate are intermittently bonded together in a first bond pattern 7 and the material layers 2,3 in the side portions 5,6 of the material laminate are intermittently bonded together in a second bond pattern 8. The percentage bonded area in relation to the total area in the two side portions 5,6 is greater than the percentage bonded area in relation to the total area of the central portion 4.

When the material laminate is used as a fluid pervious covering sheet on an absorbent article, the first material layer 2 is the layer on an absorbent article which is intended to be facing a user. For this reason, it is important that the first layer 2 has a smooth and soft surface. The first material layer 2 suitably consists of a nonwoven material. Nonwoven materials may be produced by any one of a number of methods, for instance by carding or spinning of a fibrous web which is then bonded. Further, what is known as the meltblown method may be used to depose short fibres in the form of a fibrous web. Several different ways of binding the fibres in a nonwoven material exist. For instance, different kinds of bonding agents may be used. Furthermore, heat meltable components in the material may be used with ultrasonic bonding or with heating. Other bonding methods are needling and hydroentangling. In addition, different bonding methods may be combined with each other.

The second material layer 3 may also consist of a nonwoven material. When the material laminate is intended to be used as a fluid pervious covering sheet for a sanitary napkin, the second material layer 3 is suitably a nonwoven material with a higher degree of hydrophilicity than the first material layer 2. In such an article, the second material layer 3 will suitably act as a fluid dispersion layer, at the same time diminishing rewet from the absorption body under pressure.

When the material laminate is intended to be used as a fluid pervious covering sheet for an incontinence protector or a child's diaper, the second material layer 3 preferably has a greater thickness than the first material layer and is constituted of a porous and resilient fibre material. The second material layer 3 acts as a fluid transfer layer and should have the ability to acquire large amounts of fluid in a short time, spread the fluid in the plane of the material layer, transfer the fluid to an absorption body positioned beneath the material laminate and, in addition, be able to store fluid which has not yet been absorbed by the absorption body. Particularly suitable materials for use in the second material layer are synthetic fibre wadding, carded, bonded or unbonded fibrous layers or relatively bulky nonwoven materials. Other types of suitable materials are porous hydrophilic foam materials. It is also conceivable that the second material layer consists of two or more layers of different or the same type of material.

The two material layers 2,3 are mutually bonded with a large number of bond sites 7,8. The bond sites have been formed by simultaneous compression and application of energy to the material laminate 1. Upon energy application, the thermoplastic material softens or melts at the bond sites 7,8 and thereby the two material layers 2,3 are bonded together. The bonding of the first and the second material layer 2,3 is carried out by heat bonding such as, for instance ultrasonic bonding or laser bonding. When cooling the molten or softened thermoplastic material in the laminate 1, the molten and/or softened material solidifies.

Figure 2:
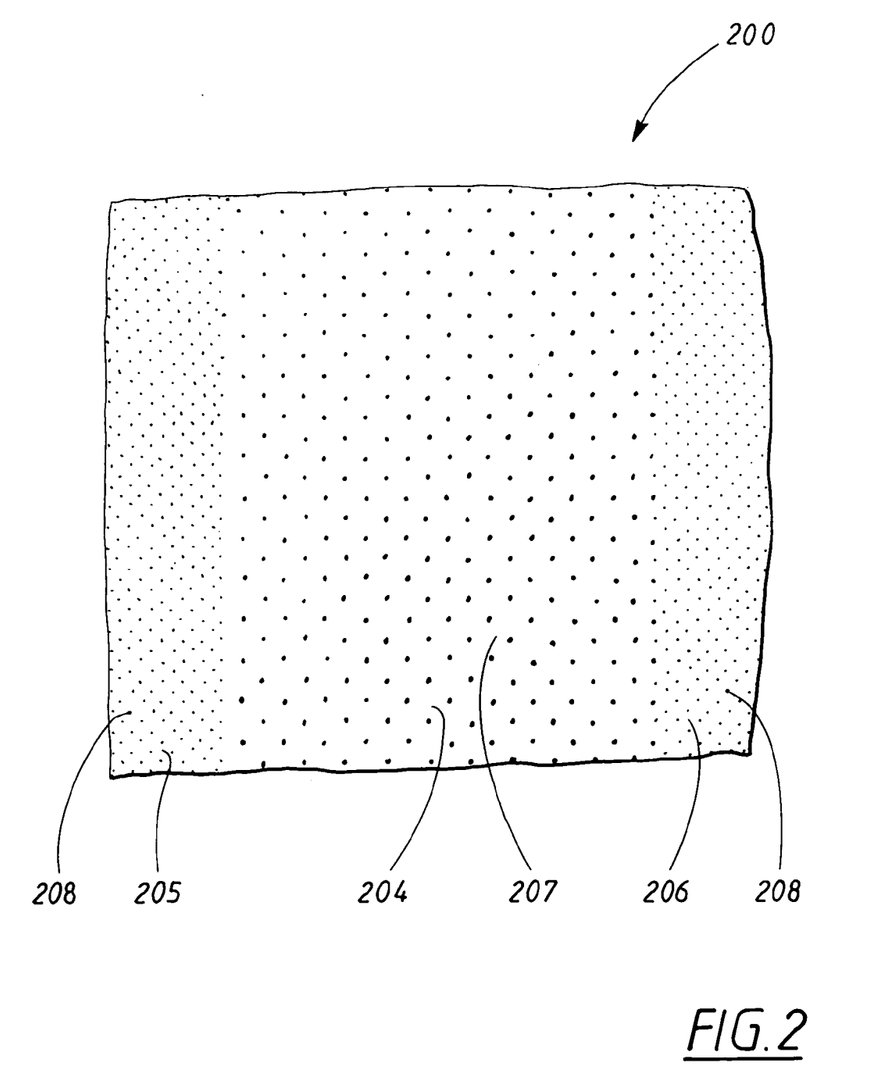
FIG. 2 shows a second bond pattern.

The material laminate 200 which is shown in FIG. 2 exhibits spot-shaped bond patterns. The material laminate 200 exhibits a first bond pattern 207 in the longitudinal central portion 204 of the article and a second bond pattern 208 in the longitudinal side portions 205,206 of the article. In the central portion 204 the spot-shaped bonds 204 in the bond pattern 207 are at a greater distance from each other than the spot-shaped bonds in the second bond pattern 208 in the two side portions 205,206. Naturally, the bond sites could have other shapes than those which have been shown in FIGS. 1 and 2. When the bond sites consist of line-shaped bond areas, this means that the smallest extension of the bond site is considerably smaller than the second extension which is perpendicular to the smallest extension. The term line-shaped bond sites does also comprise curved bond sites. Further, the first bond pattern and the second bond pattern may have the same shape or alternatively exhibit different shapes. When the bond patterns have the same shape, the bond sites in the first bond pattern are more sparsely distributed or alternatively each pattern unity in the first bond pattern is more sparsely distributed. It is also possible that each bond site in the first bond pattern occupies a smaller surface than each bond site in the second bond pattern. It is also possible, in the width direction of the material laminate, to have bond patterns exhibiting a greatest proportion of bonded area in relation to the proportion of non-bonded area closest to the longitudinal side edges of the material laminate, wherein the proportion of bonded area gradually diminishes in a direction toward the longitudinal central axis of the material laminate.

Figure 3:
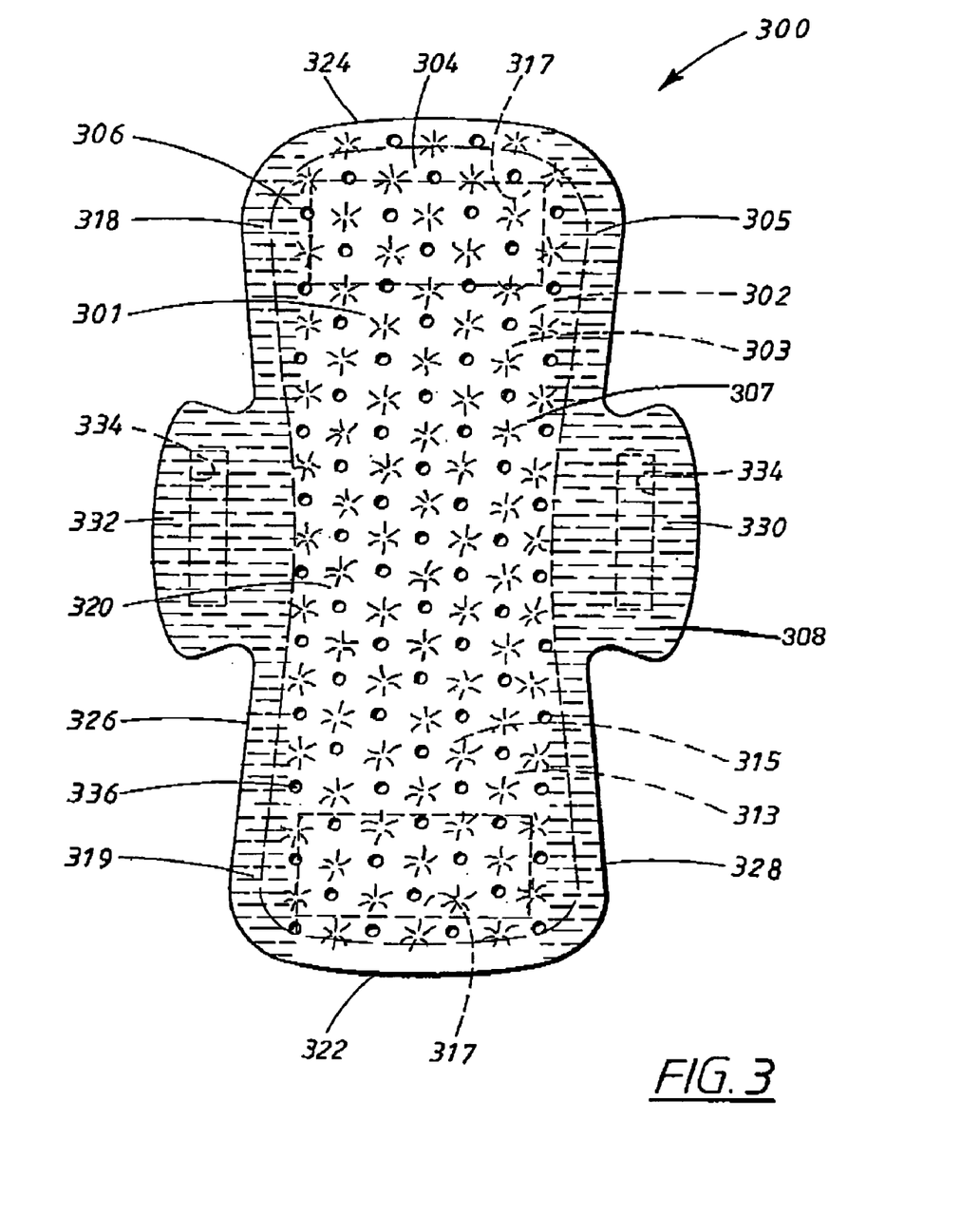
FIG. 3 shows a sanitary napkin with a material laminate in accordance with the invention.

The sanitary napkin 300, shown in FIG. 3 comprises a first fluid permeable covering sheet 301, in accordance with the invention, a fluid impermeable covering sheet 313, and an absorption body 315 enclosed between the covering sheets.

The fluid impermeable covering sheet 313 may consist of a fluid impermeable plastic film, a nonwoven sheet which has been coated with a fluid barrier material, or some other flexible sheet of material which resists fluid penetration. It is generally advantageous if the fluid impermeable covering sheet has a certain degree of breathability, i.e. will permit the passage of water vapour. The two covering sheets 301,313 have a somewhat larger extension in the plane than the absorption body 315 and extend a distance past the edges of the absorption body 315, around the entirety of its periphery. The covering sheets 301,313 are joined to each other within the protruding portions, for instance by gluing, or by welding with heat or ultrasonically. It is also possible to perform the bonding of the protruding portions simultaneously with the bonding together of the first and second material layers 302,303 of the fluid pervious covering sheet.

The absorption core 315 is usually constructed of one or more layers of cellulose fibres, for instance fluffed cellulose pulp. An example of an absorbent structure which is suitable for the purpose is found in WO 94/10956, which publication describes an absorbent material which is cut from a web of material without preceding defibration and mat-forming steps.

The material increases the surface dryness of the resulting article, which is a particular advantage when the fluid permeable covering sheet 301 has a textile sheet of material closest to the user.

In addition to cellulose fibres, the absorption core 315 may also contain superabsorbent material, i.e. material in the form of fibres, particles, granules, film or the like, which has the ability to absorb fluid corresponding to several times the weight of the superabsorbent material itself. The superabsorbent material binds the absorbed fluid and forms a fluid-containing gel. Further, the absorbent core 315 may contain binders, shape stabilising components, or the like. Additional absorption layers which improve the absorption properties may also be used, such as different types of wicking inserts, or material layers. The absorbent core 315 may be chemically or physically treated to alter the absorption properties. It is, for instance, common to arrange compressed areas in an absorption layer in order to control the fluid flow in the absorbent core. Moreover, other types of absorption materials may be utilised, alone or in combination with cellulose fibres and superabsorbent material. Some examples of useful absorbent materials are absorbent nonwoven materials, foam, or similar.

On the outside of the fluid impermeable covering sheet 313 is arranged a fastening means 317 in the form of two areas of self-adhesive glue. Before use, the adhesive areas 317 are preferably covered by removable protection sheets of release-coated paper, or plastic film, which are not shown in the drawing. A number of adhesive patterns other than the ones which are shown are, of course, conceivable, as well as other kinds of fastening means such as hook-and-loop surfaces, press-studs, girdles, special underpants, or the like. A sanitary napkin of the kind shown in FIG. 3 is attached inside an ordinary pair of underpants during use. The fastening means should naturally be of a kind which permits removal of the sanitary napkin from the underpants without causing damage thereto.

The sanitary napkin 300 exhibits somewhat wider end portions 318, 319 and a somewhat narrower crotch portion 320 located between the end portions 318, 319. The crotch portion 320 is the portion of the sanitary napkin which is intended to be placed in the user's crotch during use and serve as a receiving surface for the body fluid which is discharged to the sanitary napkin.

Furthermore, the sanitary napkin exhibits two transversely extending end edges 322,324, and two longitudinally extending side edges 326,328, running between the end edges 322,324.

The sanitary napkin is further provided with fastening flaps 330,332, which are formed of the two covering sheets 301,313 and which extend from the side edges 326,328 of the sanitary napkin 300 at the crotch portion 320. The fastening flaps 330,332 are intended to be folded around the leg edges of the user's underpants during use of the sanitary napkin 300 and to be attached to the outside of the underpants. For this purpose, the fastening flaps 330,332 are provided with special fastening means 334, which may be chosen in the same way as the fastening means 317 on the fluid impermeable covering sheet 313. Naturally, the invention can also be applied to sanitary napkins which do not exhibit any protruding fastening flaps in the crotch portion, but an advantage with such an embodiment is that the second bond pattern extends in the width direction of the article along the whole length of the fastening flaps, whereby the width of the second bond pattern will not be less than in the article's two end portions.

The fluid permeable covering sheet 301 consists of a first layer of material 302 and a second layer of material 303. The first layer of material 302 consists of a textile material, which is intended to be in contact with the body of the user when the sanitary napkin is being used. The textile material may consist of a woven or knitted cloth but is preferably a spunbond-type nonwoven material. Further, the first layer of material 302 exhibits a plurality of penetrating apertures 336. Obviously, it is also possible that the first material layer 302 exhibit apertures of different sizes. An advantage with the first material layer exhibiting penetrating apertures 336 is that the material layer can be constituted by a hydrophobic nonwoven material which is not inherently fluid permeable. Such a first material layer will remain comparatively dry even after several wettings.

The apertures may, for instance be made by means of heated needles. A heat meltable material in the first material layer 302 can, in connection with the formation of the apertures 336 in the material layer, melt in the area closest to each aperture 336. When the melted material re-solidifies after the perforation process, it forms a substantially fluid impervious edge around the entire periphery of the aperture. The continuous edge increases the tensile strength of the covering sheet and prohibits fluid from wicking from the apertures out into the cover sheet 301. Instead, body fluids that strike the sanitary napkin 300 will pass down through the covering sheet 301 to the absorption body 315 which is positioned inside the covering sheet.

The second layer of material 303 of the fluid permeable covering sheet 301 is arranged inside the first layer of material 302. The second layer of material 303 preferably consists of a material which is more hydrophilic than the first layer of material 302, whereby fluid transport between the two material layers 302,303 will take place in a direction towards the absorption body 315 of the sanitary napkin. Some examples of suitable materials are different types of nonwoven materials, air-laid or wet-laid cellulose layers, wadding of different kinds, foam materials, or the like.

The two material layers 302,303 in the covering sheet 301 are bonded together in the same manner as the material layers 2,3 in the material laminate 1 which is described in FIG. 1. Accordingly, the covering sheet 301 exhibits a first bond pattern 307 in the longitudinal central portion 304 of the article and a second bond pattern 308 in the longitudinal side portions 305,306 of the article. The first bond pattern 307 consists of line-shaped bond sites wherein five or, alternatively, six bond sites together form a star-shaped unity. Accordingly, the first bond pattern 307 consists of a plurality of star-shaped unities. The second bond pattern 308 consists of a plurality of straight line-shaped bond sites extending in the width direction of the article. When the bond sites consist of an essentially straight line, it is an advantage if the extension of the bond sites in the length direction exhibits an angle to the length direction of the article. Hence, in this manner the material layers at the side edges of the article are more efficiently prohibited from separating from each other as compared to if the extension of the bond sites in the length dimension coincides with the length direction of the article.

Figure 4:
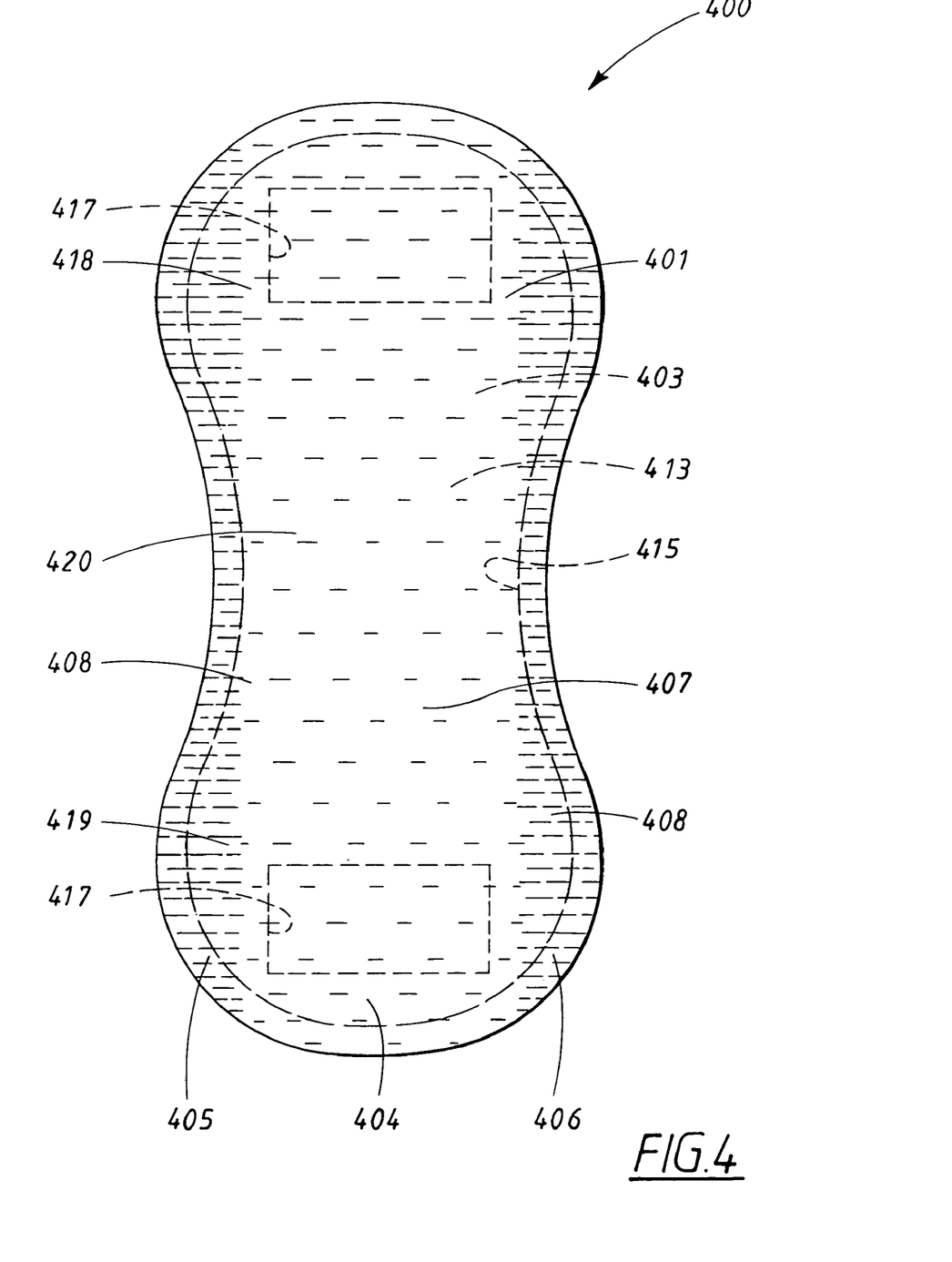
FIG. 4 shows an incontinence protector with a material laminate in accordance with the invention.

The incontinence protector 400 which is shown in FIG. 4 comprises a covering sheet 401 which is constituted by a material laminate as previously described in FIG. 1. The incontinence protector 400 has substantially the same construction as the sanitary napkin in FIG. 3. The second material layer 403 of the fluid pervious covering sheet 401 is a fluid pervious fluid transfer layer. The fluid pervious covering sheet 401 encloses together with a fluid impervious covering sheet 413 an absorption body 415. The two covering sheets 401,413 have a somewhat greater planar extension than the absorption body 415 and extend a distance out beyond the edges of the absorption body. The covering sheets 401,413 are mutually connected within the protruding portions, for instance by adhesion or ultrasonic or heat welding.

As a non-limiting example of a material laminate in accordance with the invention can be mentioned a nonwoven material composed in accordance with the invention and consisting of a first material layer 402 of a nonwoven material of synthetic fibres and a second material layer 403 of a synthetic fibrous wadding.

The absorption body 415 is constructed similarly to the absorption body 315 described for the sanitary napkin in FIG. 3. Absorption bodies for incontinence protectors usually contain more superabsorbent material than absorbent bodies for sanitary napkins. The thin absorption bodies which are usual in children's diapers and incontinence protectors of today, often consist of a compressed blended or layered structure of cellulose fluff pulp and superabsorbent material.

In the same manner as for the sanitary napkin which is described in FIG. 3, a fastening device is arranged on the outside of the fluid barrier covering sheet 413, for instance in the form of two areas of self-adhesive glue. Before use, the adhesive areas 417 are suitably covered by removable protection sheets of release-coated paper, or plastic film, which are not shown in the drawing. A number of adhesive patterns other than the ones which have been shown are, of course, conceivable.

The incontinence protector 400 exhibits somewhat wider end portions 418,419 and a somewhat narrower crotch portion 420 situated between the end portions 418,419. The crotch portion 420 is the part of the incontinence protector which, during use, is intended to be placed in the crotch of the user and serve as receiving surface for the body fluid which is excreted to the incontinence protector.

What is claimed is:

1. A material laminate for use as a covering sheet for an absorbent article with a length direction, a width direction and a thickness direction and exhibiting a central axis extending in the length direction and two opposing side edges extending in the length direction and comprising, in the thickness direction, a first fluid pervious material layer and a second fluid pervious porous material layer wherein at least one of the material layers comprises a thermoplastic material and wherein the two material layers are mutually connected by bond sites in the material laminate, within which bond sites the thermoplastic material has been caused to at least partially soften or melt and thereby bond the two material layers together, and wherein the material laminate includes two side portions extending in the length direction and each extending a distance in the width direction from a respective one of the side edges towards the longitudinal central axis of the material laminate and a central portion positioned between the side portions in the width extension of the material laminate wherein the first material layer and the second material layer in the central portion of the material laminate are intermittently bonded together in a first bond pattern and the first material layer and the second material layer in the two side portions of the material laminate are intermittently bonded together in a second bond pattern wherein the first fluid pervious material layer is a fibrous layer arranged so that an outside surface of the material laminate is fibrous and the percentage of bonded area in relation to the total area in the two side portions is greater than the percentage of bonded area in relation to the total area of the central portion;

wherein the proportion of bonded area in relation to the total area in the central portion is at least 0.5% less than the proportion of bonded area in relation to the total area in the side portions.

2. A material laminate for use as a covering sheet for an absorbent article with a length direction, a width direction and a thickness direction and exhibiting a central axis extending in the length direction and two opposing side edges extending in the length direction and comprising, in the thickness direction, a first fluid pervious material layer and a second fluid pervious porous material layer wherein at least one of the material layers comprises a thermoplastic material and wherein the two material layers are mutually connected by bond sites in the material laminate, within which bond sites the thermoplastic material has been caused to at least partially soften or melt and thereby bond the two material layers together, and wherein the material laminate includes two side portions extending in the length direction and each extending a distance in the width direction from a respective one of the side edges towards the longitudinal central axis of the material laminate and a central portion positioned between the side portions in the width extension of the material laminate wherein the first material layer and the second material layer in the central portion of the material laminate are intermittently bonded together in a first bond pattern and the first material layer and the second material layer in the two side portions of the material laminate are intermittently bonded together in a second bond pattern wherein the first fluid pervious material layer is a fibrous layer arranged so that an outside surface of the material laminate is fibrous and the percentage of bonded area in relation to the total area in the two side portions is greater than the percentage of bonded area in relation to the total area of the central portion;

wherein the proportion of bonded area in relation to the total area in the central portion is between 3% and 6% and the proportion of bonded area in relation to the total area in the side portions is between 5% and 8%.

3. A material laminate for use as a covering sheet for an absorbent article with a length direction, a width direction and a thickness direction and exhibiting a central axis extending in the length direction and two opposing side edges extending in the length direction and comprising, in the thickness direction, a first fluid pervious material layer and a second fluid pervious porous material layer wherein at least one of the material layers comprises a thermoplastic material and wherein the two material layers are mutually connected by bond sites in the material laminate, within which bond sites the thermoplastic material has been caused to at least partially soften or melt and thereby bond the two material layers together, and wherein the material laminate includes two side portions extending in the length direction and each extending a distance in the width direction from a respective one of the side edges towards the longitudinal central axis of the material laminate and a central portion positioned between the side portions in the width extension of the material laminate wherein the first material layer and the second material layer in the central portion of the material laminate are intermittently bonded together in a first bond pattern and the first material layer and the second material layer in the two side portions of the material laminate are intermittently bonded together in a second bond pattern wherein the first fluid pervious material layer is a fibrous layer arranged so that an outside surface of the material laminate is fibrous and the percentage of bonded area in relation to the total area in the two side portions is greater than the percentage of bonded area in relation to the total area of the central portion;

wherein each bond site exhibits a smallest extension and a second extension which is perpendicular to the smallest extension, wherein at least the smallest extension in the bond sites of the first bond pattern is less than 0.8 millimeters.

4. A material laminate in accordance with claim 3, wherein the smallest extension in the first bond pattern is 0.3 millimeters or less.

5. A material laminate in accordance with claim 1, wherein the bond sites comprise spot-bonds.

6. A material laminate in accordance with claim 1, wherein the first material layer is a hydrophobic nonwoven material.

7. A material laminate in accordance with claim 1, wherein the second bond pattern is denser than the first bond pattern.

8. A material laminate in accordance with claim 1, wherein the material laminate is in the form of a coherent, continuous web and that the central portion and the side portions extend continuously in the length direction of the continuous web.

9. An absorbent article exhibiting a substantially elongated shape with a length direction, a width direction and a thickness direction and exhibiting a central axis extending in the length direction and two opposing side edges extending in the length direction and comprising a fluid pervious covering sheet, a fluid impervious covering sheet and an absorption body enclosed between the two covering sheets, and wherein the absorbent article exhibits two side portions extending in the length direction and each extending in the width direction from a respective one of the side edges a distance towards the longitudinal central axis of the article and a central portion positioned between the side portions in the width direction of the article, wherein the fluid pervious covering sheet comprises a material laminate in accordance with claim 1, wherein the material laminate, in the central portion of the article exhibits the first bond pattern and the material laminate in the side portions of the absorbent article exhibits the second bond pattern.

10. An absorbent article in accordance with claim 9, wherein the length extension of the side portions in the width direction of the article is at least 4 millimeters along all of the length of the each side portion.

11. A material laminate in accordance with claim 9, wherein the absorbent article is a sanitary napkin, an incontinence protector, or a diaper.

12. An absorbent article in accordance with claim 9, wherein the second material layer is adjacent the absorption body.

13. A material laminate in accordance with claim 2, wherein the bond sites comprise spot-bonds.

14. A material laminate in accordance with claim 2, wherein the first material layer is a hydrophobic nonwoven material.

15. A material laminate in accordance with claim 2, wherein the second bond pattern is denser than the first bond pattern.

16. A material laminate in accordance with claim 2, wherein the material laminate is in the form of a coherent, continuous web and that the central portion and the side portions extend continuously in the length direction of the continuous web.

17. A material laminate in accordance with claim 3, wherein the bond sites comprise spot-bonds.

18. A material laminate in accordance with claim 3, wherein the first material layer is a hydrophobic nonwoven material.

19. A material laminate in accordance with claim 3, wherein the second bond pattern is denser than the first bond pattern.

20. A material laminate in accordance with claim 3, wherein the material laminate is in the form of a coherent, continuous web and that the central portion and the side portions extend continuously in the length direction of the continuous web.

21. An absorbent article exhibiting a substantially elongated shape with a length direction, a width direction and a thickness direction and exhibiting a central axis extending in the length direction and two opposing side edges extending in the length direction and comprising a fluid pervious covering sheet, a fluid impervious covering sheet and an absorption body enclosed between the two covering sheets, and wherein the absorbent article exhibits two side portions extending in the length direction and each extending in the width direction from a respective one of the side edges a distance towards the longitudinal central axis of the article and a central portion positioned between the side portions in the width direction of the article, wherein the fluid pervious covering sheet comprises a material laminate in accordance with claim 2, wherein the material laminate, in the central portion of the article exhibits the first bond pattern and the material laminate in the side portions of the absorbent article exhibits the second bond pattern.

22. An absorbent article exhibiting a substantially elongated shape with a length direction, a width direction and a thickness direction and exhibiting a central axis extending in the length direction and two opposing side edges extending in the length direction and comprising a fluid pervious covering sheet, a fluid impervious covering sheet and an absorption body enclosed between the two covering sheets, and wherein the absorbent article exhibits two side portions extending in the length direction and each extending in the width direction from a respective one of the side edges a distance towards the longitudinal central axis of the article and a central portion positioned between the side portions in the width direction of the article, wherein the fluid pervious covering sheet comprises a material laminate in accordance with claim 3, wherein the material laminate, in the central portion of the article exhibits the first bond pattern and the material laminate in the side portions of the absorbent article exhibits the second bond pattern.

23. An absorbent article in accordance with claim 21, wherein the length extension of the side portions in the width direction of the article is at least 4 millimeters along all of the length of the each side portion.

24. A material laminate in accordance with claim 21, wherein the absorbent article is a sanitary napkin, an incontinence protector, or a diaper.

25. An absorbent article in accordance with claim 21, wherein the second material layer is adjacent the absorption body.

26. An absorbent article in accordance with claim 22, wherein the length extension of the side portions in the width direction of the article is at least 4 millimeters along all of the length of the each side portion.

27. A material laminate in accordance with claim 22, wherein the absorbent article is a sanitary napkin, an incontinence protector, or a diaper.

28. An absorbent article in accordance with claim 22, wherein the second material layer is adjacent the absorption body.

* * * * *